US005658765A

United States Patent [19]
Noguchi et al.

[11] Patent Number: 5,658,765
[45] Date of Patent: Aug. 19, 1997

[54] XYLANASE PROCESS FOR PRODUCING THE SAME METHOD FOR THE TREATMENT OF PULP AND PRODUCTION OF XYLO-OLIGOSACCHARIDES

[75] Inventors: Yoshitaka Noguchi; Kazuko Ikeda; Eiko Masatsuji; Masahiko Seko, all of Chiba, Japan

[73] Assignee: Novo Nordisk A/S, Bagsvaerd, Denmark

[21] Appl. No.: 433,471

[22] PCT Filed: Jul. 13, 1994

[86] PCT No.: PCT/JP94/01145

§ 371 Date: Sep. 6, 1995

§ 102(e) Date: Sep. 6, 1995

[87] PCT Pub. No.: WO96/02632

PCT Pub. Date: Feb. 1, 1996

[51] Int. Cl.$^6$ ............................ C12P 19/14; C12N 9/24; C12N 1/20
[52] U.S. Cl. ..................... 435/99; 435/100; 435/101; 435/105; 435/200; 435/209; 435/252.5; 435/278
[58] Field of Search ..................... 435/100, 101, 435/105, 200, 209, 252.5, 278, 99

[56] References Cited

FOREIGN PATENT DOCUMENTS

| WO9110724 | 7/1991 | WIPO | C12N 1/22 |
| WO9118976 | 12/1991 | WIPO | C12N 9/16 |
| WO9218612 | 10/1992 | WIPO | C12N 1/20 |

OTHER PUBLICATIONS

Gruninger et al, "A Novel, Highly Thermostable D-Xylanase", Enzyme Microb. Technol., vol. 8, 309–314 (1986).
Rajaram et al, "Production and Characterization of Xylanase from Bacillus Thermoalkalophilus Grown On Agricultural Wastes", Applied Microbiology Biotechnology 34, 141–144 (1990).

Nanmori et al, "Purification and Properties of Thermostable Xylanase and B–Xylosidase Produced by a Newly Isolated Bacillus Stearothermophilus Strain", J. Bacteriol., 172, 6669–6672 (1992).

Dey et al, "Purification and Properties of Extracellular Endoxylanases from Alkalophilic Thermophilic Bacillus sp." Can. J. Microbiol., 38, 436–442 (1992).

Khasin et al, "Purification and Characterization of a Thermostable Xylanase from Bacillus Stearothermophilus T–6", Appl. Environ. Microbiol., 59, 1725–1730 (1993).

Nakamura et al "Thermophilic Alkaline Xylanase from Newly Isolated Alkaliphilic and Thermophilic Bacillus sp. Strain TAR–1", Biosci. Biotech. Biochem 58(1), 78–81, 1994.

Alam et al, "Production and Characterization of Themostable Xylanases by Thermomyces Languginosus and Thermoascus Aurantiacus Grown on Lignocelluloses, Enzyme Microb. Technol.", 1994 vol. 16, Apr.

Gupta et al, "A Thermostable Extracellular Xylanase from Alkalophilic Bacillus sp. NG–27", Biotechnology Letters, vol. 14, No. 11 (Nov.1992) pp. 1045–1046.

Okazaki et al, "Purification and Characterization of Xylanases from Alkalophilic Thermophilic Bacillus spp." Agric. Biol. Chem., 49(7), 2033–2039, 1985.

*Primary Examiner*—John W. Rollins
*Assistant Examiner*—Francisco C. Prats
*Attorney, Agent, or Firm*—Steve T. Zelson, Esq.; Valeta A. Gregg, Esq.

[57] ABSTRACT

Disclosed are novel xylanases, a process for producing the enzyme, a microorganism capable of producing the enzyme, a method for the treatment of pulp with the xylanase enzyme, and a process for producing xylose or xylo-oligosaccharide using the enzyme.

6 Claims, 4 Drawing Sheets

F I G. 3
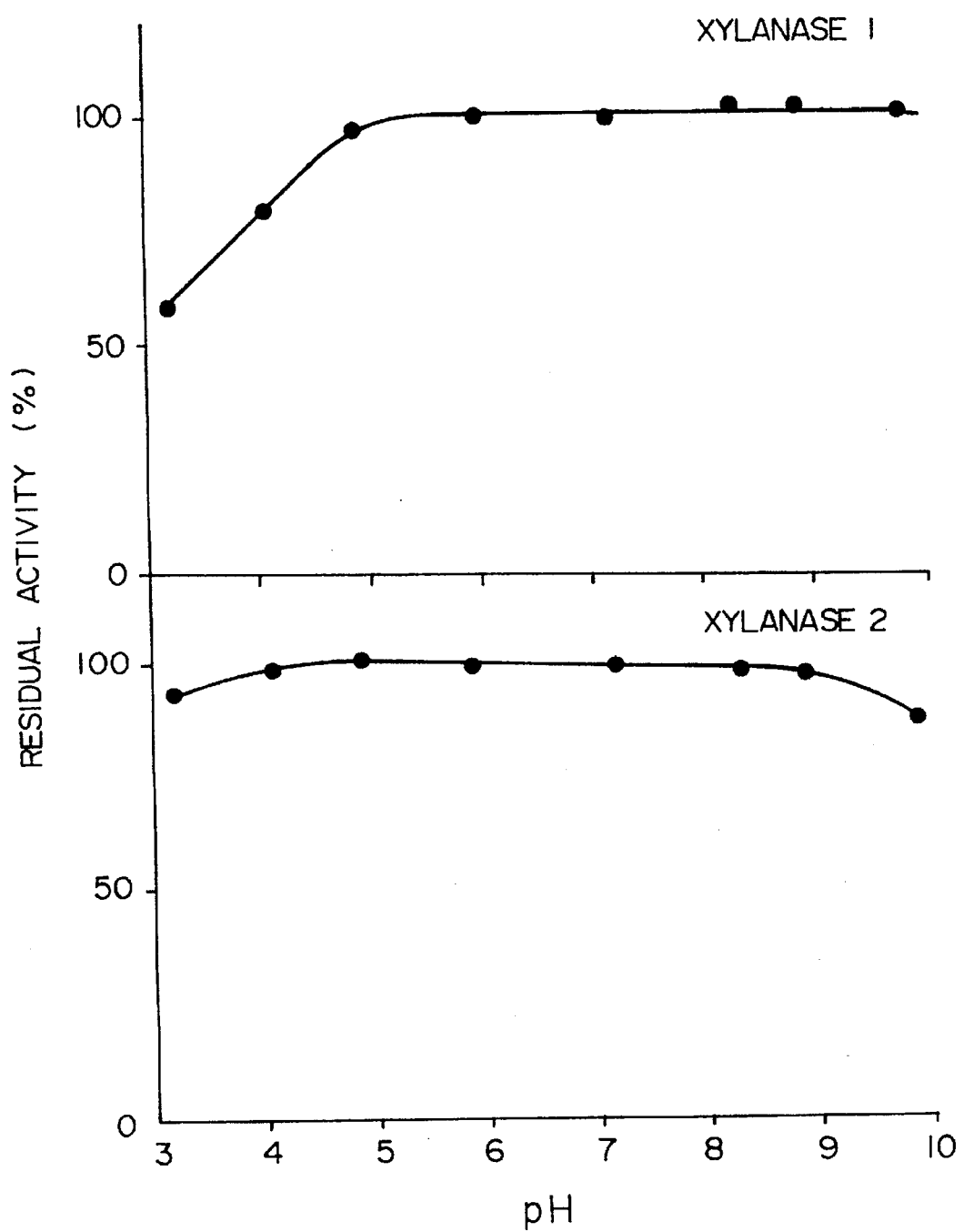

XYLANASE PROCESS FOR PRODUCING THE SAME METHOD FOR THE TREATMENT OF PULP AND PRODUCTION OF XYLO-OLIGOSACCHARIDES

TECHNICAL FIELD

The present invention relates to a novel xylanase, a process for producing the same, a microorganism producing the enzyme, a method for the treatment of pulp with the xylanase, and a process for producing xylose or xylo-oligosaccharide using the enzyme.

BACKGROUND ART

A xylanase is an enzyme which hydrolyzes xylan or xylan polysaccharides mainly composed of β-1,4-bonded-xyloses to yield its constituents, xylose and xylo-oligosaccharide. The xylanase is present widely in animals and plants. Some microorganisms can also produce xylanases. So far investigations regarding xylanase-producing microorganisms have been made on bacteria, actinomycetes, yeasts, molds and the like.

In these years, keen attention has been brought to the use of xylanases in biomass treatment. More specifically, xylanases are used in enzymatic breakdown of agricultural wastes for production of alcoholic fuels, an enzymatic treatment of animal feeds to release free sugars, an enzymatic treatment for dissolving pulp in the preparation of cellulose and an enzymatic treatment in biobleaching of pulp. In particular, xylanase has been highly expected in the paper and pulp industry wherein xylaneses are used to enhance the brightness of bleached pulp, improve the quality of pulp, decrease the amount of chlorine used in the chemical pulp bleaching steps, and to increase the freeness of pulp in the recycled paper process.

Turning to xylose, this compound is a product of xylan hydrolysis by a xylanase and widely used as a raw material of foods and drugs. Xylo-oligosaccharide which is also a product of xylan hydrolysis is expected to be for use as a sweetener or a moisturizer.

For the use in the foregoing purposes, it is desired to prepare a xylanase suitable for mass production from inexpensive raw materials and having stability to an acid, an alkali and/or heat. Up to date, however, such a xylanase has not been achieved to meet the above requirements.

DISCLOSURE OF INVENTION

An object of the present invention is to provide a novel xylanase which is thermally stable and acts stably over a wide pH range, a process for producing the xylanase, a microorganism producing the xylanase, a method for the treatment of pulp with the xylanase, and a process for producing xylose or xylo-oligosaccharide using the xylanase.

The present inventor has made extensive investigations on enzymes and microorganisms suitable for the production of a desired xylanase satisfying the requirements as stated above. As a result, it has been found that a novel microorganism belonging to the genus Bacillus can produce a novel xylanase having physicochemical properties hitherto unknown. The present invention has thus been attained.

Accordingly, a first aspect of the present invention is xylanase 1 having the following physicochemical properties:

(1) acts on xylan or a xylan polysaccharide to hydrolyze the β-1,4-xylosidic linkages in the molecule to yield xylose and xylobiose in a large quantity but to yield only in a small quantity a xylo-oligosaccharide having a polymerization degree of at least that of xylotriose;

(2) is active in the pH range of higher than 4.0 and lower than 10.0 and has the optimum pH of about 6.0;

(3) is active in the temperature range up to 90° C. and has the optimum temperature of about 75° C.;

(4) has a molecular weight of about 34,000 when determined by SDS polyacrylamide gel electrophoresis; and, (5) has an isoelectric point of about 9.4.

A second aspect of the present invention is xylanase 2 having the following physicochemical properties:

(1) acts on xylan or a xylan polysaccharide to hydrolyze the β-1,4-xylosidic linkages in the molecule to yield xylose and to yield a xylo-oligosaccharide in a large quantity;

(2) is active in the pH range of higher than 2.6 and lower than 9.6 and has the optimum pH of about 6.0;

(3) is active in the temperature range up to 90° C. and has the optimum temperature of about 65 to about 70° C.;

(4) has a molecular weight of about 21,000 when determined by SDS polyacrylamide gel electrophoresis; and, (5) has an isoelectric point of about 9.8.

A third aspect of the present invention is a process for producing a xylanase 1 or 2 which comprises culturing a microorganism belonging to the genus Bacillus and recovering the xylanase 1 or 2 from the culture medium.

A fourth aspect of the present invention is Bacillus sp. SD902 (FERM BP-4508), mutants thereof, or variants thereof obtained by Genetic engineering.

A fifth aspect of the present invention is a method for treating pulp which comprises acting a xylanase 1 or 2.

A sixth aspect of the present invention is a method for producing xylose or a xylo-oligosaccharide which comprises acting a xylanase 1 or 2.

BRIEF DESCRIPTION OF THE DRAWINGS

FIG. 3 shows graphs illustrating pH ranges in which xylanase 1 and xylanase 2 are stable.

BEST MODE FOR CARRYING OUT THE INVENTION

Figure 1:
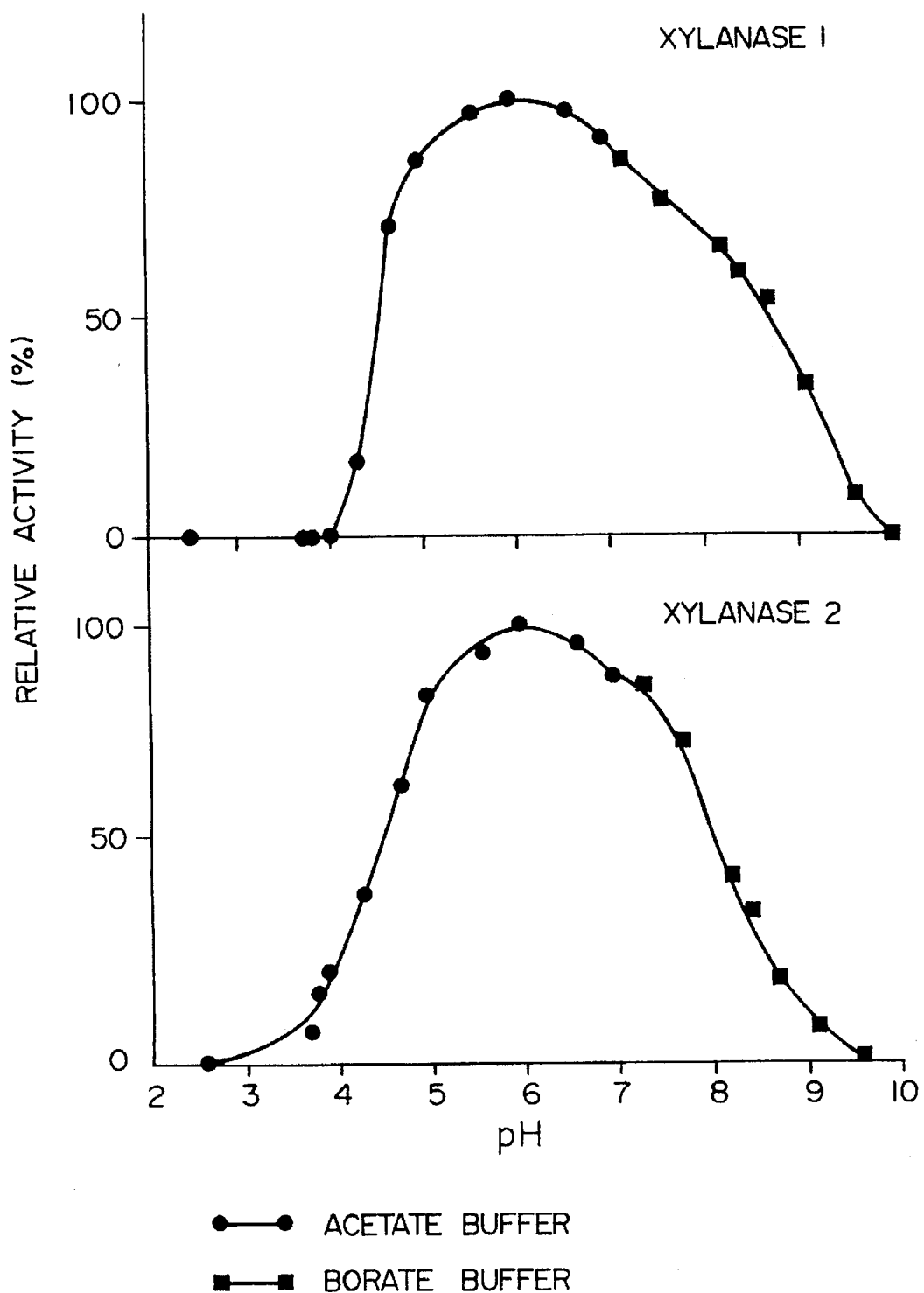
FIG. 1 shows graphs illustrating pH ranges in which xylanase 1 and xylanase 2 are active.

The microorganism used in the present invention is bacteria belonging to the genus Bacillus and capable of producing xylanase 1 and xylanase 2. The bacteria are isolated and obtained, for example, by the following procedures.

Firstly, soil samples collected from various places in Japan were cultured in a thermostat at 55° C. for 2 or 3 days on agar medium having compositions shown in Table 1 below.

TABLE 1

| Composition of Medium | |
| --- | --- |
| Oat xylan | 0.5% |
| Asparagine | 0.1% |

TABLE 1-continued

| Composition of Medium | |
|---|---|
| Yeast extract | 0.1% |
| Dipotassium hydrogenphosphate | 0.05% |
| Magnesium sulfate | 0.02% |
| Sodium chloride | 0.02% |
| Iron Sulfate | 0.002% |

Bacteria colonies around which clear plaque (i.e., hollow) appeared were isolated. Then, the strains obtained from the respective bacterial colonies were cultured for 2 days, respectively, in liquid media having compositions shown in Table 2 below, each of which was charged in a thermostat shaker at 55° C.

TABLE 2

| Composition of Medium | |
|---|---|
| Birch xylan | 1.0% |
| Polypeptone | 1.0% |
| Yeast extract | 0.1% |
| Dipotassium hydrogenphosphate | 0.5% |
| Magnesium sulfate | 0.05% |
| Sodium chloride | 0.05% |
| Iron Sulfate | 0.002% |

A xylanase activity of the culture broth was determined by the following method to select a strain showing a potent activity.

The xylanase activity was determined as follows. An enzyme solution, 0.2 ml, was mixed with 0.8 ml of 0.1M phosphate buffer (pH 7.0) containing as substrate 1.25% birch xylan (xylan derived from birch) followed by reacting them at 50° C. for 10 minutes. The reducing sugars formed were determined by the 3,5-dinitrosalicylate method. The xylanase activity described hereinafter was also determined as described above. One unit (U) is defined as the amount of enzyme that produces 1 μmol of xylose in one minute.

One of the strains thus isolated and purified is Bacillus sp. SD902 identified as described hereinafter.

The strain thus isolated, selected and purified possesses the bacteriological properties as described hereinafter, and has thus been identified as belonging to the genus Bacillus. This strain was called Bacillus sp. SD902 and was deposited with National Institute of Bioscience & Human-Technology of Industrial Science and Technology (Ibaraki-ken, Japan) on Dec. 25, 1992 and received FERM P-13356 as an accession number. Then, the deposition was transferred into an international deposition under the Budapest Treaty on Dec 22, 1993, and received FERM BP-4508 as an accession number.

The thus obtained strain, Bacillus sp. SD902, was grown at 55° C. and its bacteriological properties were examined according to the procedures described in The Genus Bacillus (1973) and Bergey's Manual of Systematic Bacteriology (1984).

(1) Morphological characteristics
 (a) Shape and size of cell: a shape of rod, size of approximately 0.4–0.8 μm×1.5–3.0 μm
 (b) Polymorphism: none
 (c) Mobility: mobile
 (d) Spore formation: spore formed, a shape of ellipse, central to subterminal location, a size of spore of approximately 0.5–0.8 μm×0.8–1.3 μm
 (e) Gram staining: positive
(2) Cultural growth condition in the following media
 (a) Bouillon-agar plate culture:
  It forms a yellowish white translucent circular colony with a flat surface.
 (b) Bouillon-agar slant culture:
  It grows spreading
 (c) Bouillon liquid culture:
  Turbid
 (d) Bouillon-gelatin stab culture: not liquefied
 (e) Litmus milk:
  Neither coagulated nor peptonized.
(3) Physiological properties
 (a) Nitrate reduction: negative
 (b) VP test: negative
 (c) VP broth pH: 5.9
 (d) Indole production: negative
 (e) Hydrogen sulfide production: negative
 (f) Starch hydrolysis: positive
 (g) Pigment production: No pigment is produced.
 (h) Catalase production: positive
 (i) Oxidase production: positive
 (k) Range of growth conditions:
  It grows in a neutral pH range (pH of 6 to 8) and at a temperature of from 25 to 60° C. but does not grow at 65° C.
 (1) Behavior toward oxygen: obligate aerobic
 (m) Denitrification reaction: negative
 (n) utilization of inorganic nitrogen sources:
  It utilizes ammonium salts but no nitrates.
 (o) Urease: negative
 (p) Utilization of citric acid: negative
 (q) OF test:
  It produces an acid anaerobically when glucose is used.
 (r) Resistance to salt:
  It grows in a NaCl concentration of 2.0%.
 (t) Existence of production of acids from the following sugars:

| 1) L-arabinose | ± |
|---|---|
| 2) D-xylose | + |
| 3) D-glucose | + |
| 4) D-mannose | + |
| 5) D-fructose | + |
| 6) D-galactose | − |
| 7) maltose | + |
| 8) sucrose | ± |
| 9) lactose | + |
| 10) trehalose | ± |
| 11) D-sorbitol | + |
| 12) D-mannitol | + |
| 13) inositol | + |
| 14) glycerine | + |
| 15) starch | − |

Based on the foregoing bacteriological properties, taxonomical search was made on the strain SD902 according to Bergey's Manual of Systematic Bacteriology (1984). Thus, it is considered that this strain belongs to the genus Bacillus in view of aerobic, gram-positive rods that form spore.

Further in view of the fact that the strain grows at temperatures above 55° C., it is considered that the strain is akin to *B. stearothermophilus*, *B. schelegelii*, *B. acidocaldarius*, *B. licheniformis*, *B. coagulans*, *B. brevis*, etc. However, the properties of anaerobic growth, VP test, VP broth pH and growth temperature range shown in Table 3 below reveal that strain SD902 has bacteriological properties dissimilar to any of these known standard bacteria belonging to the genus Bacillus.

Therefore, it is concluded based on the current taxonomy that the strain SD902 should be considered to be a new strain belonging to the genus Bacillus.

The strain, Bacillus sp. SD902, produces xylanase 1 and xylanase 2 which are novel xylanases. For example, Bacillus sp. SD902 is inoculated on liquid medium containing xylan, yeast extract and polypeptone as the major components and incubated at 55° C. for 1 to 3 days. The cultured medium is centrifuged to remove the cells and insoluble matters. The resulting culture supernatant is subjected to salting-out with

TABLE 3

|  | SD902 | acido-caldarlus | brevis | coagulans | licheni-formis | schlegelli | stearo-thermo-philus |
|---|---|---|---|---|---|---|---|
| Anaerobic growth | − | − | − | + | + | − | − |
| VP test | − | − | − | + | + | − | − |
| pH of VP broth | 5.9 | ND | 8.0–8.6 | 4.2–4.8 | 5.0–6.5 | ND | 4.8–5.8 |
| Growth temperature °C. | 25–60 | 50–65 | 10–60 | 15–60 | 15–55 | 55–65 | 30–75 |
| Growth at pH 5.7 | − | ± | ± | + | + | − | − |
| Gelatin liquefaction | − | ND | ± | − | + | − | + |
| Assimilation of starch | + | + | − | + | + | − | ± |

The microorganism used in the present invention is not limited to the aforementioned strain SD902 and any strain may be used so far as it has an ability of producing a xylanase having the properties described hereinbelow. The strain Bacillus sp. SD902 may include its spontaneous and artificial mutants, and genetically engineered variants.

Artificial mutants of Bacillus sp. SD902 can be obtained by a conventional method. For example, an original strain is subjected to artificial mutation treatment such as irradiation with ultraviolet rays or treatment with a chemical, e.g., N-methyl-N'-nitro-N-nitrosoguanidine (NTG) and then planted on an agar medium containing Oat xylan and cultivated to grow colonies. The colonies are isolated, and are then cultivated on a conventional medium for xylanase production, and the resulting xylanase is checked for identify. Thus, a strain having the most excellent productivity for the objective xylanase can be screened.

Also, genetically engineered strains can be obtained by a conventional method. For example, a presumption on DNA base sequence of the chromosome of the original strain is made based on amino acid sequence of xylanase produced by the original strain, and a characteristic portion of the presumed DNA base sequence is synthesized. Then, phosphorus atoms in the phosphoric acid groups in the sequence are labelled with radioisotope $^{32}P$. On the other hand, the entire chromosomal DNA is extracted from the original strain and digested with a suitable restriction enzyme to obtain DNA fragments, which are then subjected to Southern hybridization method to allow the chromosomal fragments to hybridize with the synthetic DNA. Thus, a chromosomal fragment which hybridizes with the synthetic DNA is screened.

The chromosomal fragment thus obtained is incorporated in a suitable vector and introduced in a xylanase non-producing strain and production of xylanase is checked. The DNA fragment of which xylanase production has been confirmed is introduced in the original strain or a strain having a higher enzyme productivity (i.e., having a higher ability of secreting proteins) using a suitable vector such as a plasmid to obtain a strain of which productivity has been improved.

ammonium sulfate, ion exchange chromatography, gel filtration chromatography and the like, in a conventional manner to isolate and/or purify xylanase 1 and xylanase 2. Xylanase 1 and xylanase 2 can be isolated from each other by, e.g., dialyzing the precipitates obtained after salting-out with ammonium sulfate, then purifying the dialysate by anionic ion exchange chromatography and cationic ion exchange chromatography and finally by gel filtration chromatography.

Physicochemical properties of xylanase 1 according to the present invention are listed below.

(1) Activity and substrate specificity:

The enzyme acts on xylan or xylan polysaccharide and hydrolyzes the β-1,4-xylosidic linkages in the molecule to yield xylose and xylobiose in large quantities but yield only in a small quantity xylo-oligosaccharides having a polymerization degree of at least that of xylotriose. Xylanase 1 does not have any substantial avicelase activity for degrading crystalline cellulose or any substantial CMCase activity for breakdown of carboxymethyl cellulose.

(2) Acting pH and the optimum pH:

When the xylanase activity is determined at 60° C. using acetate buffer or borate buffer having various pH values of from 2.5 to 10.0, xylanase 1 acts in the pH range of higher than 4.0 and lower than 10.0 and has the optimum pH at about 6.0, as shown in FIG. 1. The enzyme shows more than 70% activity of the maximum activity in the pH range of about 4.7 to about 8.0, as shown in FIG. 1.

Figure 2:
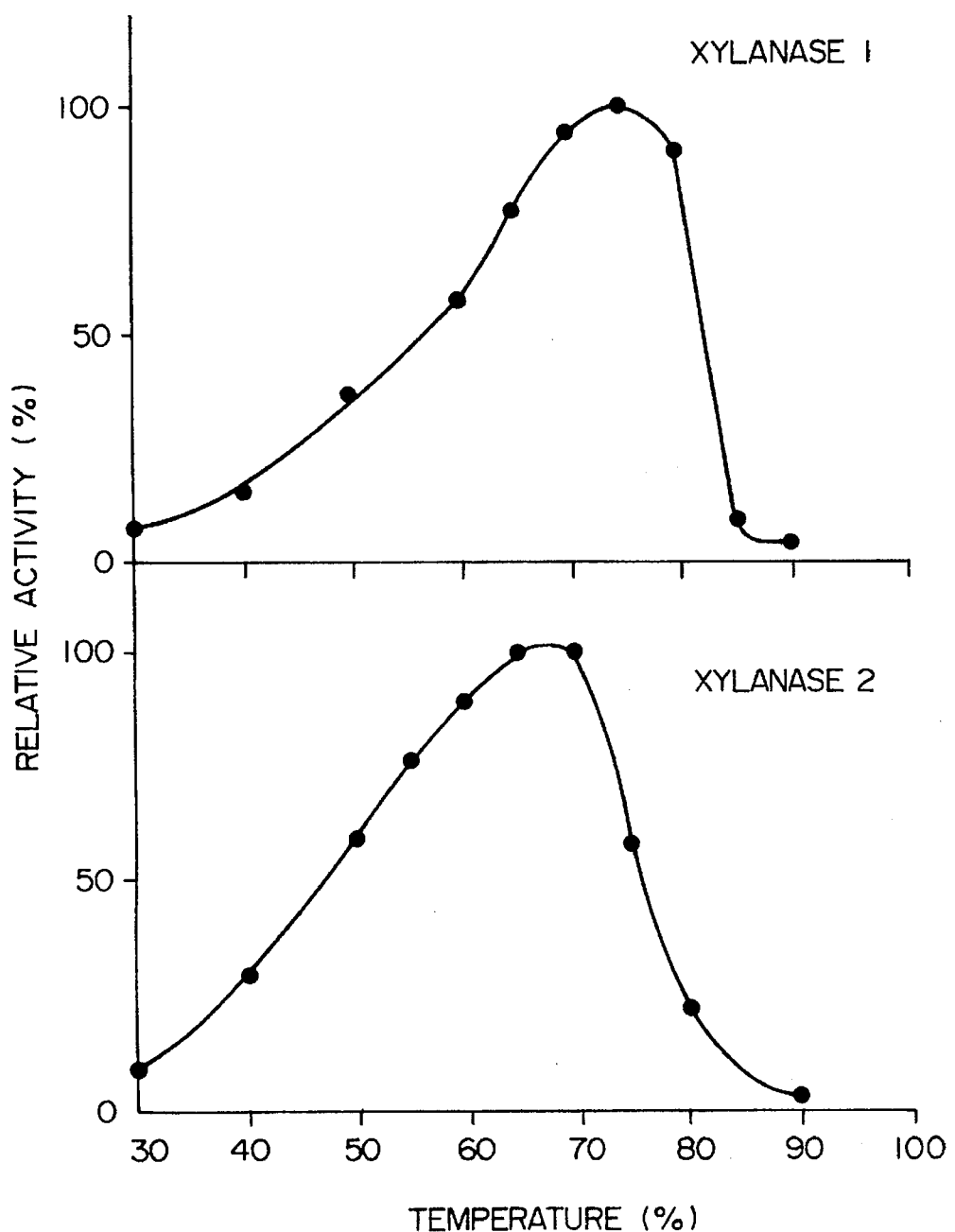
FIG. 2 shows graphs illustrating temperature ranges in which xylanase 1 and xylanase 2 are active.

(3) Acting temperature and the optimum temperature:

When the xylanase activity is determined at various temperatures ranging from 30° C. to 90° C. using phosphate buffer (pH 7.0), xylanase 1 acts in the temperature range up to 90° C. and has the optimum temperature at about 75° C., as shown in FIG. 2.

(4) pH stability:

When the xylanase activity is determined after maintaining at 40° C. for 48 hours in acetate buffer, phosphate buffer or borate buffer having various pH values in the range of 3.2 to 9.9, the enzyme retains more than 95% of the activity in the pH range of 5.0 to 9.9, as shown in FIG. 3.

Figure 4:
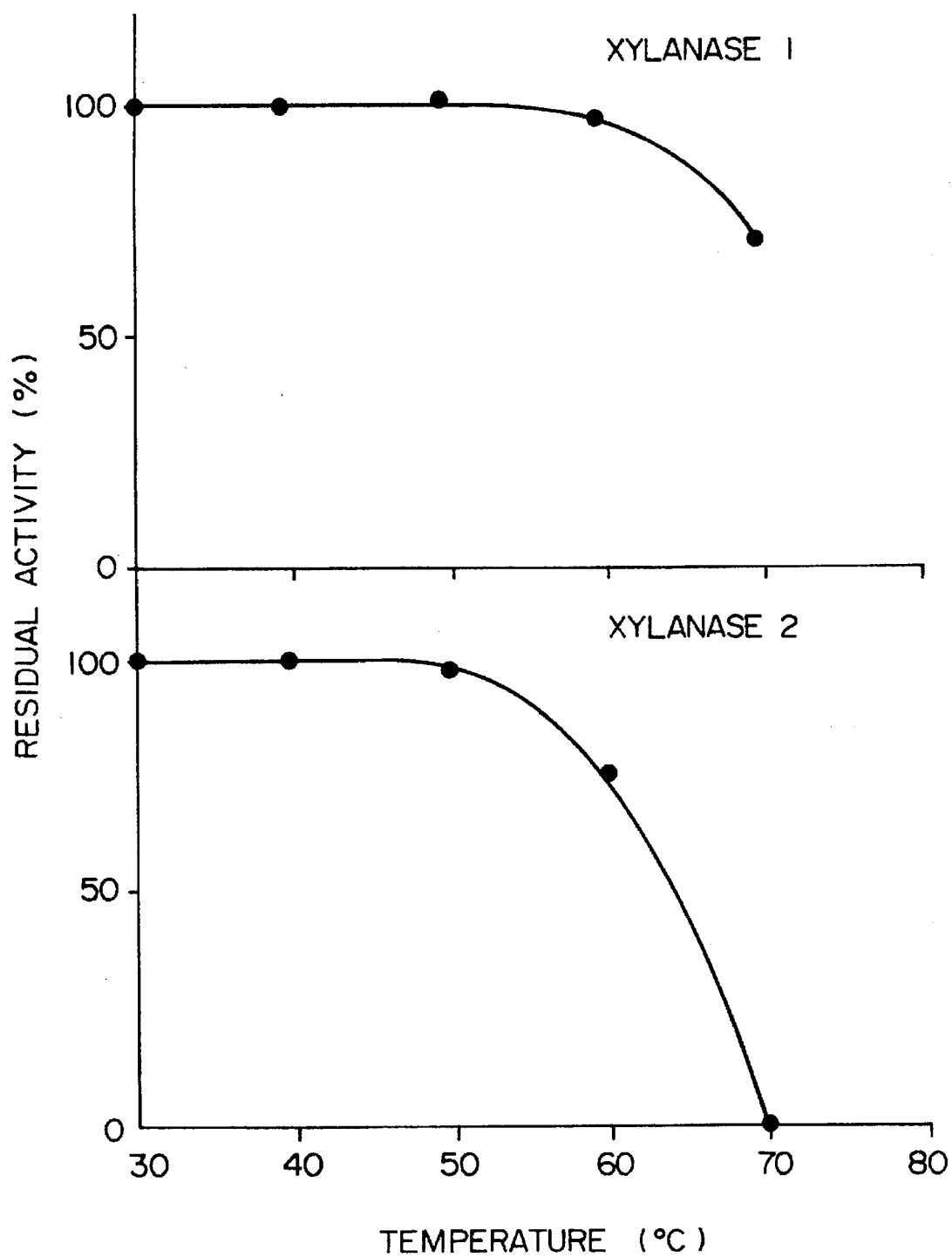
FIG. 4 shows graphs illustrating temperature ranges in which xylanase 1 and xylanase 2 are stable.

(5) Thermal stability:

When the xylanase activity is determined after maintaining at 60° C. for 24 hours in phosphate buffer (pH 7.0), the enzyme retains more than 90% of the activity, as shown in FIG. 4.

(6) Molecular weight:

The molecular weight is about 34,000 based on SDS polyacrylamide gel electrophoresis.

(7) Isoelectric point:

The enzyme has the isoelectric point at pH of about 9.4.

Physicochemical properties of xylanase 2 according to the present invention are listed below.

(1) Activity and substrate specificity:

The enzyme acts on xylan or xylan polysaccharide and hydrolyzes the β-1,4-xylosidic linkages in the molecule to yield xylose and also yield in a large quantity xylo-oligosaccharides such as xylobiose, xylotriose, xylotetraose, etc. Xylanase 2 does not have any substantial avicelase activity for degrading crystalline cellulose or any substantial CMCase activity for breakdown of carboxymethyl cellulose.

(2) Acting pH and the optimum pH:

When its xylanase activity is determined at 60° C. using acetate buffer or borate buffer having various pH values of from 2.6 to 9.6, xylanase 2 acts in the pH range of higher than 2.6 and lower than 9.6 and has the optimum pH at about 6.0. The enzyme shows more than 70% activity of the maximum activity in the pH range of about 5.0 to about 7.7.

(3) Acting temperature and the optimum temperature:

When the xylanase activity is determined at various temperatures ranging from 30° C. to 90° C. using phosphate buffer (pH 7.0), xylanase 2 acts in the temperature range up to 90° C. and has the optimum temperature at about 65° C. to 70° C.

(4) pH stability:

When the xylanase activity is determined after maintaining at 40° C. for 48 hours in acetate buffer, phosphate buffer or borate buffer having various pH values in the range of 3.2 to 9.9, the enzyme retains more than 95% of the activity in the pH range of 4.0 to 9.0.

(5) Thermal stability:

When the xylanase activity is determined after maintaining at 60° C. for 24 hours in phosphate buffer (pH 7.0), the enzyme retains more than 70% of the activity.

(6) Molecular weight:

The molecular weight is about 21,000 based on SDS polyacrylamide gel electrophoresis.

(7) Isoelectric point:

The enzyme has the isoelectric point at pH of about 9.8.

Xylanase 1 or xylanase 2 can be produced by culturing Bacillus sp. SD902, mutants thereof, or variants thereof by genetic engineering, and recovering the produced xylanase 1 or xylanase 2 from the culture broth.

For culturing, conventional methods of culturing bacteria may be used and typical examples include liquid culture and solid culture. Among others, aerobic liquid culture is preferable from an economic viewpoint. Representative examples of such culturing are aerial spinner culturing and shake culturing, under aerobic conditions.

Any medium may be employed for the production of xylanases of the present invention so long as the strain used can proliferate. As carbon sources, carbonaceous compounds that can be assimilated or those containing the same may be used, for example, various xylans; various raw materials containing xylan or xylan polysaccharides such as wheat bran, pulp wastes, saccharified crop lees or rice straws; glucose, starch or starch hydrolysates such as liquefied starch; sugars such as molasses, solely or as admixture thereof.

As nitrogen sources, there may be used nitrogen compounds that can be assimilated or those containing the same; for example, there may be used, singly or in combination, organic nitrogen-containing compounds such as various amino acids, corn steep liquor, maltose extract, peptone, soybean powders and defatted soybean powders; and inorganic nitrogen compounds such as ammonium salts, e.g., ammonium chloride and ammonium sulfate.

Media may also appropriately contain other additives, if necessary, such as various organic and inorganic materials required for growth of the bacteria and for production of the enzymes, or compounds containing these materials, e.g., salts such as phosphates, magnesium salts, calcium salts and manganese salts; vitamins, yeast extract, and the like.

The temperature for incubation may generally be in the range of 10 to 70° C., and preferably in the range of 25 to 60° C., more preferably in the range of 35 to 55° C., for the strain sp. SD902. The pH for incubation may generally be in the range of 4 to 10 throughout the entire phase of incubation but preferably in the range of 6 to 8 for the strain sp. SD902. The time period for incubation is generally for 10 to 120 hours. The incubation is stopped at the time when the amount of xylanases accumulated reaches the maximum. For the strain sp. SD902, the time period from 20 to 80 hours is preferable particularly from an economic aspect.

After completion of the incubation, xylanase 1 or xylanase 2 can be recovered from the culture broth in a conventional manner. That is, the culture broth is appropriately subjected to conventional operations selected from precise filtration such as filter press filtration, membrane filtration, centrifugation, ammonium sulfate precipitation, concentration through membrane, drying, etc. to remove unnecessary matters from the culture broth. Then xylanase 1 or xylanase 2 can be harvested as the enzyme solution or in the form of powders. For example, the cells in the culture broth are removed by centrifugation. The resulting supernatant can be used as it is. Alternatively, the supernatant may be diluted or concentrated appropriately, or added with a stabilizer and the resulting solution may be used as the enzyme solution. Further alternatively, the enzyme is precipitated from the supernatant with, e.g., 60% ammonium sulfate and the precipitates are filtered in a conventional manner to obtain the enzyme. The thus obtained enzyme may be dialyzed overnight and the dialysate is applied to various ion exchange chromatographies or gel filtration chromatography in a conventional manner to obtain xylanase 1 or xylanase 2.

Xylanase 1 and xylanase 2 of the present invention do not substantially possess the cellulase activity for hydrolyzing cellulose as the major constituent of pulp. Accordingly, these enzymes are suitable to enhance the brightness of pulp, to improve the quality of paper, to decrease the amount of chemical bleaching agents such as chlorine used in the pulp bleaching stages, and to treat pulp for other purposes, without inducing any damage of cellulose in pulp.

Where xylanase 1 or xylanase 2 is used for these pulp treatments, pulp is treated with the enzyme in the amount of 0.01 to 1000 U/g dry pulp, preferably 0.05 to 10 U/g dry pulp.

In the pulp treatment according to the present invention, conditions of the enzymes for treating pulp, such as temperature, pH, pressure, time period, etc., may be suitably chosen so that the desired enzymatic action is exhibited to achieve the desired effects such as enhancement of the brightness. For example, the temperature may be in the range of 10 to 80° C., preferably 40 to 70 ° C. The pH may be in the range of 3 to 10, preferably 4 to 9, more preferably 5 to 8.

The pressure may be applied under such a pressure conventionally used for pulp bleaching or other ordinary pulp treating steps; there is no particular restriction but normal pressure is preferably from an economic standpoint. The time period for the treatments may be in the range of 10 minutes to 50 hours, preferably 1 to 24 hours, more preferably 1 to 5 hours.

As will be shown below in the Examples, when unbleached Kraft pulp from broadleaf trees is treated with 500 U/kg dry pulp of xylanase derived from Bacillus sp. SD902, the lignin contained in the pulp is removed in large amounts by the treatment in a relatively short period of time. Furthermore, in the case where it is desired to enhance the brightness, the amount of a chemical bleaching agent used after the enzymatic treatment can be greatly reduced. It is considered that the pulp treatment of the present invention which provides the effects described above is sufficient as a substitute for at least a part of the current bleaching process using chlorine bleaching agents.

The method of the present invention for treating pulp is applicable to a wide range of pulp derived from a broadleaf tree, a needle-leaf tree or a non-tree material, such as kraft pulp, sulfite pulp, semi-chemical pulp, groundwood pulp, refiner groundwood pulp, thermo-mechanical pulp, etc. By applying the pulp treatment method of the present invention to these pulps, the amount of lignin remained in pulp can be reduced to attain the effects such as enhancement of the brightness of pulps, improvement of the quality, and decrease of the amount of a chemical bleaching agent. The pulp treatment method of the present invention may also be applied to the bleaching steps of these pulps by oxygen or the like, prior to or after the bleaching.

Following the pulp treatment using the xylanases of the present invention, an extraction may also be carried out to effectively remove the lignin dissolved or susceptible to be dissolved out of the pulp. The extraction may be performed using, e.g., sodium hydroxide. In this case, typical conditions for the extraction are set forth to have a pulp concentration of 0.3 to 20%, a sodium hydroxide concentration of 0.5 to 5% based on the weight of dry pulp, a temperature range of 40 to 80° C., and a time period for 30 minutes to 3 hours, preferably for 1 to 2 hours.

After pulp is treated according to the method of the present invention, a chemical bleaching agent may also be used to further enhance the brightness of the pulp. In this case, even if the amount of the chemical bleaching agent is greatly decreased as compared to the case of bleaching pulp only with the chemical bleaching agent, a better brightness can be obtained. Where chlorine dioxide is used as a chemical bleaching agent, its amount can be reduced by 23% to 43% or even more.

When paper is made from the pulp so treated according to the method of the present invention, it has been found that the paper has excellent properties such as a lower content of chlorinated phenol compounds, as compared to paper prepared from conventional bleached pulp. It is considered to be because xylan, which is one of the hemicellulose components in pulp, would be efficiently removed by the treatment with the xylanase having no cellulase activity. However, the details of the mechanism are yet unknown.

The present invention also provides a method for producing xylose or xylo-oligosaccharides such as xylobiose, xylotriose, xylotetraose and the like which comprises acting xylanase 1 or xylanase 2 on xylan or xylan polysaccharides.

According to the method of the present invention, xylose or xylo-oligosaccharides may be produced using xylanase 1 or xylanase 2, under such conditions that the enzyme retains the xylanase activity. For example, the temperature for the treatment is in the range of about 10° to about 80° C., preferably 40° to 70° C.; the pH for the treatment is in the range of 3 to 10, preferably 4 to 9, more preferably 5 to 8. The reaction time is set to such a period that the enzyme acts on xylan or xylan polysaccharides, for example, in the range of 10 minutes to 24 hours, preferably 1 to 10 hours, more preferably 1 to 3 hours.

As the xylan or xylan polysaccharides used to produce xylose or xylo-oligosaccharides according to the present invention, there may be used agricultural wastes, e.g., rice straws, bagasse, wheat bran, corn cob; woods, or xylans previously isolated therefrom. These xylan or xylan polysaccharides may be used in a concentration of 0.1 to 50%, preferably 0.5 to 30% in weight.

Xylanase 1 and xylanase 2 of the present invention do not substantially possess the cellulase activity which hydrolyzes cellulose. Accordingly, in the case of producing xylose or xylo-oligosaccharides, the enzyme is used in the range of 0.01 to 1000 U/g dry xylan, preferably 0.05 to 10 U/g dry xylan.

The present invention is described in more detail by referring to the examples. However, these examples are merely illustratively shown but the present invention is not deemed to be limited the examples.

EXAMPLE 1

In a 5-liter volume jar fermenter was charged 2 liters of liquid medium (pH 7.0) composed of 1.0% birch xylan, 0.1% yeast extract, 1.0% polypeptone, 0.5% dipotassium hydrogenphosphate, 0.05% magnesium sulfate, 0.002% iron sulfate and 0.05% sodium chloride, which was then sterilized at 121° C. for 20 minutes. The cells of Bacillus sp. SD902 cultured in 100 ml of the same medium were inoculated on the liquid medium followed by aerobic stirred culturing at 55° C. for 48 hours with stirring at a stirring speed of 1000 rpm in an aerial amount of 1 liter/min. After the incubation, the culture broth was centrifuged at 6000 rpm to remove the cells.

Ammonium sulfate was then added to 700 ml of the resulting supernatant to reach the 60% saturation for salting-out. The enzyme precipitates obtained by the salting-out were dissolved in 50mM phosphate buffer (pH 7.0). The solution was dialyzed overnight. After the dialysis, the enzyme solution was applied to anionic ion exchange chromatography (DEAE-Cellulofine, manufactured by Seikagaku Kogyo K. K.). The fraction passed through was then applied to cationic ion exchange chromatography (CM-Cellulofine, manufactured by Seikagaku Kogyo K. K.). Thereafter elution was performed at a linear gradient of 1000 ml sodium chloride of 0 to 0.6M to fractionate by 7 ml each. The fraction at which the xylanase activity was noted was collected and concentrated by ultra-filtration. From the concentrate, 10 ml was taken and purified by gel filtration chromatography (Toyo Pearl HW55s, manufactured by Toso Co., Ltd.) using 5 mM phosphate buffer (pH 7.0) as an eluent. Xylanase 1 (810 U) was obtained as the fraction eluted earlier and xylanase 2 (1150 U) as the fraction eluted later.

EXAMPLE 2

To 0.5 wt % solution of birch xylan (manufactured by Sigma Inc., X-0502) was added xylanase 1 obtained in a manner similar to Example 1 in an amount of 200 U/g xylan. After pH was adjusted to 6.0, the mixture was heated to 60° C. to cause the reaction. The time course of the reaction was monitored up to 24 hours. After the reaction was completed, the reaction mixture was treated at 100° C. for 5 minutes, the reaction mixture was centrifuged to remove the enzyme precipitates. The reaction product was analyzed by thin layer chromatography and high performance liquid chromatography.

The analysis of the product by thin layer chromatography was performed as follows. The reaction product was developed on a thin layer (Kieselgel 60F254, manufactured by Merck Co.) with butanol: pyridine: water =8:1:1. As a color developer, a 5:1 mixture by volume of an acetone solution containing 0.2% diphenylamine and 0.2% aniline to 85% phosphoric acid was used. As the result of analysis, the production of xylose and xylobiose was noted from the beginning of the reaction. At the later stage of the reaction, xylose and xylobiose produced were markedly increased.

The analysis of the reaction product by high performance liquid chromatography was performed as follows. The reaction product was applied to Shodex Ionpak S-801 (manufactured by Showa Denko K.K.) as a gel filtration column for sugars, which was eluted with water for chromatographic treatment. The eluted component was detected with a differential refractometer. The analysis of the product obtained after the reaction for 24 hours reveals that 22% (w/w) xylose and 40% (w/w) xylobiose were produced based on the starting birch xylan.

EXAMPLE 3

The reaction and analysis were conducted in a manner similar to Example 2, except that 200 U/g xylan of xylanase 2 obtained in a manner similar to Example 1 was added to 0.5 wt % solution of birch xylan (manufactured by Sigma, X-0502). As the result of analysis, the production of xylose and xylobiose was noted from the beginning of the reaction. At the later stage of the reaction, xylose and xylobiose produced were markedly increased. The analysis of the product obtained after the reaction for 24 hours reveals that 8% (w/w) xylose, 34% (w/w) xylobiose and 7% (w/w) xylo-oligosaccharides having a polymerization degree of at least that of xylotriose were produced based on the starting birch xylan.

EXAMPLE 4

The enzyme-containing supernatant prepared from the culture broth of Bacillus sp. SD902 obtained in a manner similar to Example 1 was added to 500 g (50 g as dry pulp) of broadleaved unbleached kraft pulp slurry having a pulp concentration of 10 wt %, as the xylanase activity, in an amount of 100, 500 or 1000 U/kg dry pulp. In the enzymatic treatment, the pH was adjusted to 6. The pulp slurry was heated at 60° C. for an hour or for 3 hours. After filtering, the pulp was washed with 2-to 3-fold amount of water. Thereafter water was added to the pulp so that the mixture was obtained to have a pulp concentration of 10 wt % and to contain sodium hydroxide corresponding to 1.3 wt % based on the weight of dry pulp. The mixture was extracted at 60° C. for an hour followed by washing the pulp with water.

An enzyme-free sample was prepared in a manner similar to the above except that no enzyme was added. The effect of the enzymatic treatment was compared with the sample. The kappa number used as an index of lignin content was determined according to the Japanese Industrial Standards JIS P8211. The kappa numbers of the pulp obtained by the treatments are shown in Table 4. The weight of dry pulp after the enzymatic treatment for 3 hours showed 49 g.

TABLE 4

| Time for Enzymatic Treatment | Amount of Enzyme (U/kg pulp) | Kappa Number |
|---|---|---|
| 1 | 0 | 12.5 |
| 1 | 100 | 10.7 |
| 1 | 500 | 10.2 |
| 1 | 1000 | 10.0 |
| 3 | 0 | 12.5 |
| 3 | 100 | 10.5 |
| 3 | 500 | 10.1 |
| 3 | 1000 | 10.0 |

EXAMPLE 5

The enzymatic treatment and extraction with sodium hydroxide were carried out in a manner similar to Example 4 except for using 500 g (50 g as dry pulp) of needle-leaved unbleached kraft pulp slurry having a pulp concentration of 10 wt %. An enzyme-free sample was also prepared in a manner similar to Example 4. The kappa numbers of the pulp obtained by these treatments are shown in Table 5. The weight of dry pulp after the enzymatic treatment for 24 hours showed 49 g.

TABLE 5

| Time for Enzymatic Treatment | Amount of Enzyme (U/kg pulp) | Kappa Number |
|---|---|---|
| 1 | 0 | 21.8 |
| 1 | 100 | 19.8 |
| 1 | 500 | 19.6 |
| 1 | 1000 | 19.5 |
| 3 | 0 | 21.8 |
| 3 | 100 | 19.6 |
| 3 | 500 | 19.5 |
| 3 | 1000 | 19.4 |

Comparative Example 1

Chlorine dioxide was added to broadleaved unbleached kraft pulp slurry having a pulp concentration of 10 wt % in 12.5 kg/t dry pulp. The mixture was heated at 70° C. for an hour. After the bleaching, the mixture was washed with 2- to 3-fold amount of water. Then water was added to the pulp so that the mixture had a pulp concentration of 10 wt % and sodium hydroxide corresponding to 1.3 wt % based on the weight of dry pulp was added. The mixture was extracted at 60° C. for an hour and the pulp was then washed with water. The kappa number of the pulp was 3.5.

Water was added to the thus obtained pulp extracted with sodium hydroxide (kappa number of 3.5) so that the mixture was made to have a pulp concentration of 10 wt % and to contain 18.9 kg of chlorine dioxide/t dry pulp. The mixture was heated at 70° C. for 3 hours and the pulp were then washed with 2- or 3-fold amount of water. The pulp was dried and the bleached pulp had the Hunter brightness of 90%. The Hunter brightness was determined by the Japanese Industrial Standards JIS P8123. The total amount of chlorine dioxide used in the two-stage bleaching was 31.4 kg/t dry pulp.

EXAMPLE 6

The enzyme-containing supernatant prepared from the culture broth of Bacillus sp. SD902 obtained in a manner similar to Example 1 was added to 500 g (50 g as dry pulp) of broadleaved unbleached kraft pulp slurry having a pulp concentration of 10 wt %, as the xylanase activity, in an amount of 500 U/kg dry pulp. In the enzymatic treatment, the pH was adjusted to 6. The pulp slurry was heated at 60° C. for 3 hours. After filtering, the pulp was washed with 2- to 3-fold amount of water. Thereafter water was added to the pulp so that the mixture was made to have a pulp concentration of 10 wt % and to contain 10.2 kg of chlorine dioxide/t dry pulp. The mixture was heated at 70° C. for an hour. The pulp was then washed with 2- or 3-fold amount of water. Water was then added to the pulp so that the mixture had a pulp concentration of 10 wt % and sodium hydroxide corresponding to 1.3 wt % based on the weight of dry pulp was added. The mixture was extracted at 60° C. for an hour and the pulp was then washed with water. The kappa number of the pulp was 3.5.

Water was added to the thus obtained pulp (kappa number of 3.5) enzyme-treated, chlorine dioxide-treated and then sodium hydroxide-extracted so that the mixture was made to have a pulp concentration of 10 wt % and to contain 7.7 kg of chlorine dioxide/t dry pulp. The mixture was heated at 70° C. for 3 hours and the pulp was then washed with 2- or 3-fold amount of water. The pulp was dried and the bleached pulp had the Hunter brightness of 90%. The total amount of chlorine dioxide used in the two stage bleaching was 17.9 kg/t dry pulp. The amount of chlorine dioxide used was less by 43% than Comparative Example 1 where no enzyme was used.

EXAMPLE 7

Xylanase 1 obtained in a manner similar to Example 1 was added to 500 g (50 g as dry pulp) of broadleaved unbleached kraft pulp slurry having a pulp concentration of 10 wt %, in an amount of 500 U/kg dry pulp as the xylanase activity. In the enzymatic treatment, the pH was adjusted to 6. The pulp slurry was heated at 60° C. for 3 hours. After filtering, the pulp was washed with 2- to 3-fold amount of water. Thereafter water was added to the pulp so that the mixture was made to have a pulp concentration of 10 wt % and to contain 10.1 kg of chlorine dioxide/t dry pulp. The mixture was heated at 70° C. for an hour. The pulp was then washed with 2- or 3-fold amount of water. Water was then added to the pulp so that the mixture had a pulp concentration of 10 wt % and sodium hydroxide corresponding to 1.3 wt % based on the weight of dry pulp was added. The mixture was extracted at 60° C. for an hour and the pulp was then washed with water. The kappa number of the pulp was 3.5.

Water was added to the thus obtained pulp (kappa number of 3.5) enzyme-treated, chlorine dioxide-treated and then sodium hydroxide-extracted so that the mixture was made to have a pulp concentration of 10 wt % and to contain 7.7 kg of chlorine dioxide/t dry pulp. The mixture was heated at 70° C. for 3 hours and the pulp was then washed with 2- or 3-fold amount of water. The pulp was dried and the bleached pulp had the Hunter brightness of 90%. The total amount of chlorine dioxide used in the two stage bleaching was 17.8 kg/t dry pulp. The amount of chlorine dioxide used was less by 43% than Comparative Example 1 where no enzyme was used.

EXAMPLE 8

Xylanase 2 obtained in a manner similar to Example 1 was added to 500 g (50 g as dry pulp) of broadleaved unbleached kraft pulp slurry having a pulp concentration of 10 wt %, in an amount of 500 U/kg dry pulp as the xylanase activity. The pulp slurry was heated at 60° C. for 3 hours. After filtering, the pulp was washed with 2- to 3-fold amount of water. Thereafter water was added to the pulp so that the mixture was made to have a pulp concentration of 10 wt % and to contain 11.3 kg of chlorine dioxide/t dry pulp. The mixture was heated at 70° C. for an hour. The pulp was then washed with 2- or 3-fold amount of water. Water was then added to the pulp so that the mixture had a pulp concentration of 10 wt % and sodium hydroxide corresponding to 1.3 wt % based on the weight Of dry pulp was added. The mixture was extracted at 60° C. for an hour and the pulp was then washed with water. The kappa number of the pulp was 3.5.

Water was added to the thus obtained pulp (kappa number of 3.5) enzyme-treated, chlorine dioxide-treated and then sodium hydroxide-extracted so that the mixture was made to have a pulp concentration of 10 wt % and to contain 12.9 kg of chlorine dioxide/t dry pulp. The mixture was heated at 70° C. for 3 hours and the pulp was then Washed with 2- or 3-fold amount of water. The pulp was dried and the bleached pulp had the Hunter brightness of 90%. The total amount of chlorine dioxide used in the two state bleaching was 24.2 kg/t dry pulp. The amount of chlorine dioxide used was less by 23% than Comparative Example 1 where no enzyme was used.

EXAMPLE 9

The enzyme-containing supernatant prepared from the culture broth of Bacillus sp. SD902 obtained in a manner similar to Example 1 was added to 500 g (50 g as dry pulp) of broadleaved unbleached kraft pulp slurry having a pulp concentration of 10 wt %, as the xylanase activity, in an amount of 500 U/kg dry pulp. In the enzymatic treatment, the pH was adjusted to 6. The pulp slurry was heated at 60° C. for 3 hours. After filtering, the pulp was washed with 2- to 3-fold amount of water. Thereafter water was added to the pulp so that the mixture was made to have a pulp concentration of 10 wt % and to contain 10.2 kg of chlorine dioxide/t dry pulp. The mixture was heated at 70° C. for an hour. After the bleaching, the pulp was washed with 2- or 3-fold amount of water. Water was then added to the pulp so that the mixture was made to have a pulp concentration of 10 wt % and to contain sodium hydroxide corresponding to 1.3 wt % based on the weight of dry pulp. The mixture was extracted at 60° C. for an hour followed by washing the pulp with water. The kappa number of the pulp showed 3.5. On the other hand, pulp showing the kappa number of 3.5 were obtained in a manner similar to Comparative Example 1, using no enzyme.

Water was added to the thus obtained pulp having the kappa number of 3.5 so that the mixture was made to have a pulp concentration of 10 wt % and to contain 8.0 kg of chlorine dioxide/t dry pulp. The mixture was heated at 70° C. for 3 hours and the pulp was then washed with 2- or 3-fold amount of water. After drying, the Hunter brightness was determined. As the result, the Hunter brightness of the enzyme-treated pulp was 90.2%, whereas the Hunter brightness of the enzyme-untreated pulp was 88.5%.

EXAMPLE 10

Xylanase 1 obtained in a manner similar to Example 1 was added to 500 g (50 g as dry pulp) of broadleaved unbleached kraft pulp slurry having a pulp concentration of 10 wt %, in an amount of 500 U/kg dry pulp as the xylanase activity. The pulp slurry was heated at 60° C. for 3 hours.

After filtering, the pulp was washed with 2- to 3-fold amount of water. Thereafter water was added to the pulp so that the mixture was made to have a pulp concentration of 10 wt % and to contain 10.1 kg of chlorine dioxide/t dry pulp. The mixture was heated at 70° C. for an hour. The pulp was then washed with 2- or 3-fold amount of water. Water was then added to the pulp so that the mixture had a pulp concentration of 10 wt % and sodium hydroxide corresponding to 1.3 wt % based on the weight of dry pulp was added. The mixture was extracted at 60° C. for an hour and the pulp was then washed with water. The kappa number of the pulp was 3.5. On the other hand, pulp showing the kappa number of 3.5 was obtained in a manner similar to Comparative Example 1, using no enzyme.

Water was added to the thus obtained pulp having the kappa number of 3.5 so that the mixture was made to have a pulp concentration of 10 wt % and to contain 8.0 kg of chlorine dioxide/t dry pulp. The mixture was heated at 70° C. for 3 hours and the pulp was then washed with 2- or 3-fold amount of water. After drying, the Hunter brightness was determined. As the result, the Hunter brightness of the enzyme-treated pulp was 90.2%, whereas the Hunter brightness of the enzyme-untreated pulp was 88.0%.

EXAMPLE 11

Xylanase 2 obtained in a manner similar to Example 1 was added to 500 g (50 g as dry pulp) of broadleaved unbleached kraft pulp slurry having a pulp concentration of 10 wt %, in an amount of 500 U/kg dry pulp as the xylanase activity. The pulp slurry was heated at 60° C. for 3 hours. After filtering, the pulp was washed with 2- to 3-fold amount of water. Thereafter water was added to the pulp so that the mixture was made to have a pulp concentration of 10 wt % and to contain 11.3 kg of chlorine dioxide/t dry pulp. The mixture was heated at 70° C. for an hour. The pulp was then washed with 2- or 3-fold amount of water. Water was then added to the pulp so that the mixture had a pulp concentration of 10 wt % and sodium hydroxide corresponding to 1.3 wt % based on the weight of dry pulp was added. The mixture was extracted at 60° C. for an hour and the pulp was then washed with water. The kappa number of the pulp was 3.5. On the other hand, pulp showing the kappa number of 3.5 was obtained in a manner similar to Comparative Example 1, using no enzyme.

Water was added to the thus obtained pulp having the kappa number of 3.5 so that the mixture was made to have a pulp concentration of 10 wt % and to contain 12.0 kg of chlorine dioxide/t dry pulp. The mixture was heated at 70° C. for 3 hours and the pulp was then washed with 2- or 3-fold amount of water. After drying, the Hunter brightness was determined. As the result, the Hunter brightness of the enzyme-treated pulp was 89.8%, whereas the Hunter brightness of the enzyme-untreated pulp was 89.0%.

Industrial Applicability

According to the present invention, there are provided xylanase 1 and xylanase 2 which are novel enzymes, as well as the process for producing the enzymes. These novel xylanases are effectively employed for biomass treatments, e.g., to enhance the brightness of pulp, to improve the quality, to decrease the amount of a chemical bleaching agent in the pulp bleaching stages and to increase the freeness of pulp. The present invention also provides the method for such pulp treatments. By such pulp treatments according to the present invention, large quantities of the lignin can be removed by the enzymatic treatment in a relatively short period of time, resulting in the enhanced brightness of pulp, the improved quality, the decreased amount of a chemical bleaching agent, etc. The novel xylanases of the present invention are efficiently utilized to prepare xylose or xylo-oligosaccharides widely used as sweeteners, moisturizers, feeds, etc. in the food industry, cosmetic industry and feed industry. According to the present invention, there are also provided the method of preparing xylose or xylo-oligosaccharides. The present invention also provides the bacteria belonging to the genus Bacillus that can produce these novel xylanases.

We claim:

1. An isolated xylanase having the following physicochemical properties:
   (A) acts on a xylan molecule to hydrolyze β-1,4-xylosidic linkages in the molecule to yield more xylose and xylobiose than a xylo-oligosaccharide having a polymerization degree of at least that of xylotriose;
   (B) is active in the pH range of higher than 4.0 and lower than 10.0 and has an optimum pH of about 6.0;
   (C) is active in a temperature range up to 90° C. and has an optimum temperature of about 75° C.;
   (D) has a molecular weight of about 34,000 as determined by SDS polyacrylamide gel electrophoresis; and
   (E) has an isoelectric point of about 9.4,
wherein said xylanase is obtained by culturing Bacillus sp. SD902 (FERM BP-4508) or mutants having all the identifying characteristics thereof, and recovering the xylanase from the culture medium.

2. An isolated xylanase having the following physicochemical properties:
   (A) acts on a xylan molecule to hydrolyze β-1,4-xylosidic linkages in the molecule to yield xylose and a xylo-oligosaccharide;
   (B) is active in the pH range of higher than 2.6 and lower than 9.6 and has an optimum. pH of about 6.0;
   (C) is active in a temperature range up to 90° C. and has an optimum temperature of about 65 to about 70° C.;
   (D) has a molecular weight of about 21,000 as determined by SDS polyacrylamide gel electrophoresis; and,
   (E) has an isoelectric point of about 9.8
wherein said xylanase is obtained by culturing Bacillus sp. SD902 (FERM BP-4508) or mutants having all the identifying characteristics thereof, and recovering the xylanase from the culture medium.

3. A process for producing an isolated xylanase which comprises the steps of:
   (A) culturing a microorganism belonging to the genus Bacillus, and
   (B) recovering a xylanase having the following physicochemical properties:
      (a) (i) acts on a xylan molecule to hydrolyze β-1,4-xylosidic linkages in the molecule to yield more xylose and xylobiose than xylo-oligosaccharide having a polymerization degree of at least that of xylotriose;
      (ii) is active in the pH range of higher than 4.0 and lower than 10.0 and has an optimum pH of about 6.0;
      (iii) is active in a temperature range up to 90° C. and has an optimum temperature of about 75° C.;
      (iv) has a molecular weight of about 34,000 as determined by SDS polyacrylamide gel electrophoresis; and
      (v) has an isoelectric point of about 9.4, or recovering a xylanase having the following physiochemical properties:

(b)(i) acts on a xylan molecule to hydrolyze β-1,4-xylosidic linkages in the molecule to yield xylose and a xylo-oligosaccharide;

(ii) is active in the pH range of higher than 2.6 and lower than 9.6 and has an optimum pH of about 6.0;

(iii) is active in a temperature range up to 90° C. and has an optimum temperature of about 65 to about 70° C.;

(iv) has a molecular weight of about 21,000 as determined by SDS polyacrylamide gel electrophoresis; and, (v) has an isoelectric point of about 9.8 wherein said microorganism belonging to the genus Bacillus is a Bacillus sp. SD902 (FERM BP-4508) bacteria and or mutants having all of the identifying characteristics thereof.

4. A biologically pure culture of Bacillus sp. SD902 (FERM BP-4508) or mutants having all of the identifying characteristics thereof.

5. A method for treating pulp which comprises the step of contacting pulp with an isolated xylanase having the following physicochemical properties:

(a) (i) acts on a xylan molecule to hydrolyze β-1,4-xylosidic linkages in the molecule to yield more xylose and xylobiose than xylo-oligosaccharide having a polymerization degree of at least that of xylotriose;

(ii) is active in the pH range of higher than 4.0 and lower than 10.0 and has an optimum pH of about 6.0;

(iii) is active in a temperature range up to 90° C. and has an optimum temperature of about 75° C.;

(iv) has a molecular weight of about 34,000 as determined by SDS polyacrylamide gel electrophoresis; and (v) has an isoelectric point of about 9.4, or with an isolated xylanase having the following physiochemical properties:

(b)(i) acts on a xylan molecule to hydrolyze β-1,4-xylosidic linkages in the molecule to yield xylose and a xylo-oligosaccharide;

(ii) is active in the pH range of higher than 2.6 and lower than 9.6 and has an optimum pH of about 6.0;

(iii) is active in a temperature range up to 90° C. and has an optimum temperature of about 65 to about 70° C.;

(iv) has a molecular weight of about 21,000 as determined by SDS polyacrylamide gel electrophoresis; and (v) has an isoelectric point of about 9.8, wherein said xylanase is obtained by culturing Bacillus sp. SD902 (FERM BP4508) or mutants having all the identifying characteristics thereof, and recovering the xylanase from the culture medium.

6. A method for producing xylose which comprises the step of contacting xylan with an isolated xylanase having the following physicochemical properties:

(a)(i) acts on a xylan molecule to hydrolyze β-1,4-xylosidic linkages in the molecule to yield more xylose and xylobiose than xylo-oligosaccharide having a polymerization degree of at least that of xylotriose;

(ii) is active in the pH range of higher than 4.0 and lower than 10.0 and has an optimum pH of about 6.0;

(iii) is active in a temperature range up to 90° C. and has an optimum temperature of about 75° C.;

(iv) has a molecular weight of about 34,000 as determined by SDS polyacrylamide gel electrophoresis; and (v) has an isoelectric point of about 9.4, or with an isolated xylanase having the following physiochemical properties:

(b) (i) acts on a xylan molecule to hydrolyze β-1,4-xylosidic linkages in the molecule to yield xylose and a xylo-oligosaccharide;

(ii) is active in the pH range of higher than 2.6 and lower than 9.6 and has an optimum pH of about 6.0;

(iii) is active in a temperature range up to 90° C. and has an optimum temperature of about 65 to about 70° C.;

(iv) has a molecular weight of about 21,000 as determined by SDS polyacrylamide gel electrophoresis; and (v) has an isoelectric point of about 9.8, wherein said xylanase is obtained by culturing Bacillus sp. SD902 (FERM BP-4508) or mutants having all the identifying characteristics thereof, and recovering the xylanase from the culture medium.

* * * * *